(12) United States Patent  
Murakami (10) Patent No.: US 8,734,333 B2  
(45) Date of Patent: May 27, 2014

(54) ENDOSCOPE SYSTEM, ENDOSCOPE VIDEO PROCESSOR AND METHOD OF DRIVING ENDOSCOPE SYSTEM

(75) Inventor: Hiroshi Murakami, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 667 days.

(21) Appl. No.: 12/717,695

(22) Filed: Mar. 4, 2010

(65) Prior Publication Data

US 2010/0240953 A1 Sep. 23, 2010

(30) Foreign Application Priority Data

Mar. 18, 2009 (JP) .................................. 2009-066380
Mar. 18, 2009 (JP) .................................. 2009-066381

(51) Int. Cl.
*A62B 1/06* (2006.01)

(52) U.S. Cl.
USPC ........................................................ 600/160

(58) Field of Classification Search
USPC ............................... 348/68; 362/574; 600/180
See application file for complete search history.

(56) References Cited

U.S. PATENT DOCUMENTS

| | | | | |
|---|---|---|---|---|
| 6,099,466 | A * | 8/2000 | Sano et al. ..................... | 600/160 |
| 7,043,291 | B2 * | 5/2006 | Sendai ........................... | 600/478 |
| 7,479,990 | B2 | 1/2009 | Imaizumi et al. | |
| 7,959,338 | B2 * | 6/2011 | Kazakevich ................... | 362/574 |
| 2002/0013512 | A1 * | 1/2002 | Sendai et al. ................. | 600/160 |
| 2002/0026099 | A1 | 2/2002 | Adachi et al. | |
| 2002/0177751 | A1 * | 11/2002 | Ueno et al. .................... | 600/160 |
| 2004/0109478 | A1 | 6/2004 | Korn | |
| 2008/0091065 | A1 * | 4/2008 | Oshima et al. ................ | 600/109 |
| 2009/0059359 | A1 * | 3/2009 | Nahm et al. ................... | 359/368 |
| 2009/0062617 | A1 * | 3/2009 | Mizuyoshi .................... | 600/178 |
| 2009/0118578 | A1 * | 5/2009 | Takasugi et al. ............. | 600/109 |
| 2009/0194781 | A1 * | 8/2009 | Harada .......................... | 257/98 |

FOREIGN PATENT DOCUMENTS

EP 2 074 934 A2 7/2009
JP 2007-202589 A 8/2007

OTHER PUBLICATIONS

European Search Report dated Jul. 12, 2010.

* cited by examiner

*Primary Examiner* — Philip R Smith
(74) *Attorney, Agent, or Firm* — McGinn IP Law Group, PLLC (57) ABSTRACT

A light source device emits normal illumination light and special illumination light interchangeably at a charge-storage time of an imaging device. A DRP is reconfigurable between a normal image producing circuit and a special image producing circuit. A CPU instructs the reconfiguration of the DRP when detecting that a vertical synchronization signal from a drive circuit falls to zero level. The DRP gains an access to a configuration memory to load circuit information of the normal or special image producing circuit. According to the circuit information loaded, the DRP changes functions and interconnection of processor elements.

19 Claims, 8 Drawing Sheets

ENDOSCOPE SYSTEM, ENDOSCOPE VIDEO PROCESSOR AND METHOD OF DRIVING ENDOSCOPE SYSTEM

BACKGROUND OF THE INVENTION

1. Field of the Invention

The present invention relates to an endoscope system, an endoscope video processor and a method of driving the endoscope system for internal examination using normal light and special light, such as white light and infrared light.

2. Description of Related Art

Endoscopic examination is widely used in a medical field. A typical electronic endoscope has a CCD image sensor, or a similar imaging device, at a distal end of an insertion section to be inserted into the body of a patient. The electronic endoscope is connected to an endoscope video processor and a light source device by means of a cable and connectors.

The endoscope video processor applies various types of processing to an image signal of the imaging device, and produces an internal body image, which is displayed on a monitor for medical diagnosis. The light source device has a white light source, such as a xenon lamp, and provides illumination light to the electronic endoscope.

In the medical endoscopic examination, an imaging technique called NBI (Narrow Bandwidth Imaging) is used to facilitate the detection of disease. In the NBI, a diseased site is illuminated by narrow bandwidth light (hereinafter, special illumination light), instead by spectrally broad white light (hereinafter, normal illumination light), and its reflected light is imaged (the resultant image is hereinafter referred to as a special image, in distinction from a normal image produced with the normal illumination light). This NBI technique allows for obtaining images that highlight submucosal blood vessels or that highlight stomach wall, intestine tissue or other internal organs.

In some cases, a filter turret that combines sectors for normal illumination light and special illumination light is introduced across an illumination light path. This filter turret is moved mechanically by a motor or the like upon a switching operation from a doctor (operator) to obtain the normal image and the special image at substantially the same time.

Also, Japanese Patent Laid-open Publication No. 2007-202589 discloses an electronic endoscope apparatus configured to rotate a filter turret at predetermined time intervals (for example, one filed interval) to place a wide-bandwidth sector (for normal illumination light) and a narrow-bandwidth sector (for special illumination light) interchangeably in the illumination light path. The wide-bandwidth (or normal) image and the narrow-bandwidth (or special) image thus obtained are processed in a wide-bandwidth image processing circuit and a narrow-bandwidth image processing circuit respectively. As a result, the normal and special images can be displayed at substantially the same time (one field difference), and compared with each other in diagnosis.

The above electronic endoscope apparatus needs to have separate image processing circuits because the normal and special images require different types of image processing. Unfortunately, however, two image processing circuits in a single processor results in increasing the component cost and power consumption. Additionally, the size of the apparatus is increased.

In view of this, U.S. Pat. No. 7,479,990 B2 (corresponding to Japanese Patent Laid-open Publication No. 2005-013611) discloses a processor having an FPGA (Field Programmable Gate Array), as an image processing circuit, which can change the circuit configuration programmably in accordance with circuit data. The circuit information for normal images is loaded to the FPGA when the normal images are going to be obtained, and the circuit information for special images is loaded to the FPGA when the special images are going to be obtained. This allows the normal and special images to be processed with this single FPGA. Now, the processor only needs a single processing circuit (or FPGA) for image processing, and is thus able to offer small sizing and low cost.

Additionally, as being configured to execute the wide-bandwidth image processing and the narrow-bandwidth image processing alternately, the FPGA enables to display the normal and special images side by side. The FPGA, however, takes long time to reconfigure the circuit arrangement, and it is difficult to switch between the normal image processing and the special image processing at a substantially short interval, such as one filed or one frame.

Even worse, the FPGA is not able to execute the image processing during the load of the circuit data. The above-mentioned processor is therefore equipped with a bypass circuit for processing the image signals to display monochrome images on the monitor while the FPGA is loading the circuit data. Because of this FPGA problem of unable to provide different types of images at one-filed or one-frame intervals, the FPGA cannot accomplish so-called simultaneous observation for visualizing the normal and special images simultaneously.

SUMMARY OF THE INVENTION

In view of the foregoing, it is an object of the present invention to provide an endoscope system, an endoscope video processor and a method of driving the endoscope system which can enable simultaneous observation of normal and special images while reducing a circuit size and manufacturing cost.

In order to achieve the above and other objects, an endoscope system according to the present invention includes an imaging device, a light source device, a dynamically reconfigurable processor and a display device. The imaging device captures an image of a site of interest, and generates image signal. The light source device interchangeably emits at least first and second illumination light having different spectral characteristics at charge-storage time intervals of the imaging device. The dynamically reconfigurable processor has a reconfigurable region to be reconfigured between first and second image producing circuits in synchronization with interchange of the illumination light. The first image producing circuit processes the image signal obtained under the first illumination light to produce a first image, and the second image producing circuit processes the image signal obtained under the second illumination light to produce a second image. The display device displays the first and second images next to each other.

The dynamically reconfigurable processor preferably has a common region which applies common processing to the image signals regardless of the type of the illumination light. This common region includes a display control section for displaying the first and second images on the display device.

The dynamically reconfigurable processor has a plurality of processor elements whose functions and interconnections are dynamically changeable, and a configuration memory that stores multiple sets of circuit information which defines different functions and interconnections of the processor elements. The reconfigurable region and the common region are both configured by selecting one of the circuit information and determining the function and interconnection of the processor elements.

The dynamically reconfigurable processor resets internal data of the processor elements in the reconfigurable region after the reconfiguration.

Preferably, a reconfiguration controller is further provided for determining the timing of the reconfiguration. The reconfiguration controller instructs the reconfiguration and/or resetting of the internal data during vertical blanking intervals.

In particular, the reconfiguration controller instructs the reconfiguration and/or resetting of the internal data in response to one of a drive signal for the imaging device and a light switching signal of the illumination light.

In one aspect of the invention, the endoscope system further includes an optical splitter for separating the illumination light, and a wavelength detector for detecting a wavelength of the separated illumination light. In this instance, the reconfiguration controller instructs the reconfiguration and/or resetting of the internal data in response to change in wavelength of the illumination light that the wavelength detector detects.

In another aspect of the invention, the reconfiguration controller instructs the dynamically reconfigurable processor to configure the reconfigurable region into a different circuit for different processing during the reconfiguration between the first and second image processing circuits.

In another aspect of the invention, the light source device includes a first laser source for emitting a first laser beam having a first wavelength as its center wavelength, a second laser source for emitting a second laser beam having a second wavelength shorter than the first wavelength as its center wavelength, an optical path combiner an optical path combiner for combining optical paths of the first and second laser beams, an optical fiber for transmitting the first and second laser beams out of the optical path combiner, a first wavelength conversion element disposed near an exit end of the optical fiber, and a second wavelength conversion element disposed ahead of the exit end of the optical fiber. The first wavelength conversion element is excited by the first laser beam to emit first laser-induced luminescence. The second wavelength conversion element is excited by the second laser beam to emit second laser-induced luminescence having a longer wavelength than the second wavelength in a certain visible spectrum. The first laser beam is combined with the first laser-induced luminescence to create white light as the first illumination light, and the second laser-induced luminescence composes special illumination light as the second illumination light.

In this instance, the first laser source is turned on in a normal image capturing session using the first illumination light, and the second laser source is turned on in a special image capturing session using the second illumination light.

In another aspect of the invention, the light source device may have a normal light source for normal illumination light as the first illumination light and a special light source for special illumination light as the second illumination light.

Alternatively, the light source device may include a light source, a filter turret and a filter driver. The light source emits the light containing wavelength components of normal illumination light as the first illumination light and special illumination light as the second illumination light. The filter turret has one or more normal illumination light transmission sectors and one or more special illumination light transmission sectors. The filter turret is disposed in a rotatable manner in an optical path of the illumination light in the light source. The filter driver rotates the filter turret in synchronization with charge-storage time intervals of the imaging device.

An endoscope video processor according to the present invention includes the dynamically reconfigurable processor and the reconfiguration controller. The reconfiguration controller preferably instructs the reconfiguration during vertical blanking intervals.

A method of driving the endoscope system according to the present invention includes a light emitting step, an imaging step, a reconfiguration step and a displaying step. In the light emitting step, different types of illumination light are emitted interchangeably at charge-storage time intervals of an imaging device of an endoscope to illuminate a site of interest. In the imaging step, the images of the site of interest are captured under the illumination light with the imaging device. In the reconfiguration step, a reconfigurable region of a dynamically reconfigurable processor is reconfigured among several image processing circuits every time the illumination light is interchanged so as to produce differently illuminated images. In the displaying step, at least two of these images corresponding to the types of the illumination light are displayed next to each other on a display device. Preferably, the reconfiguration step is performed during vertical blanking intervals.

According to the present invention, the single processor applies appropriate image processing to a plurality of image signals obtained under different types of illumination light having different spectral characteristics, and produces differently illuminated images at substantially the same time. It is therefore possible to enable the simultaneous observation of different images, and to reduce the circuit size and the manufacturing cost.

The reconfiguration is performed in the vertical blanking intervals, and continuity is maintained between the images.

The reconfigurable region and the common region are both configured by defining the functions of processor elements and a connection among these processor elements. This enables the single processor to perform a series of operations from image processing to display control, and allows for further reduction of the circuit size. Additionally, high-speed processing is possible because there is no data transmission to external devices during the image processing.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENTS

Figure 1:
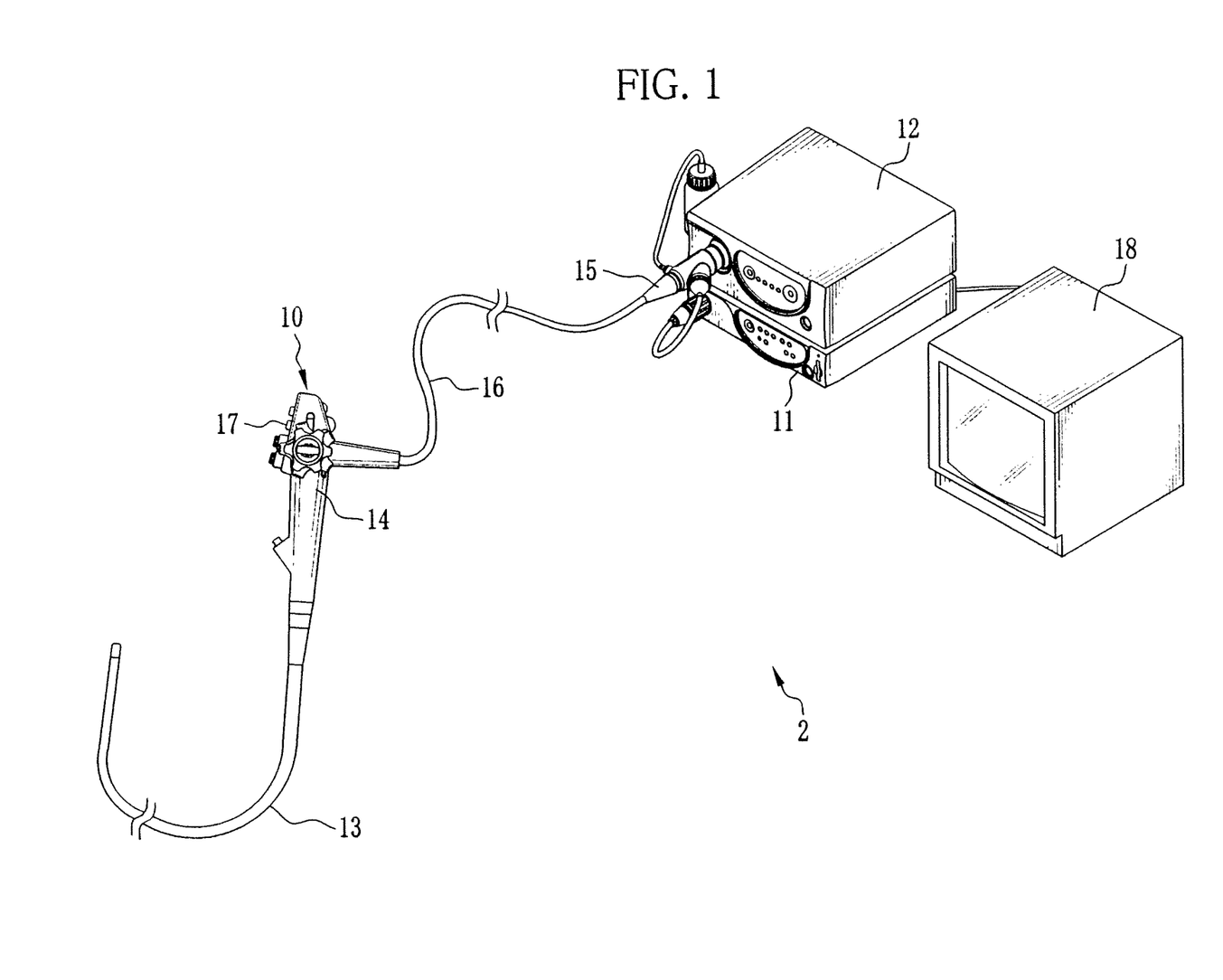
FIG. 1 is an external view of an endoscope system according to the present invention.

Referring to FIG. 1, an endoscope system 2 includes an electronic endoscope 10, an endoscope video processor 11 and a light source device 12. As well known, the electronic endoscope 10 has a flexible insertion section 13 to be inserted into the body of a patient, a handling section 14 linked to a proximal end of the insertion section 13, a connector 15 to be plugged to the endoscope video processor 11 and the light source device 12, and a universal cord 16 between the handling section 14 and the connector 15.

Figure 2:
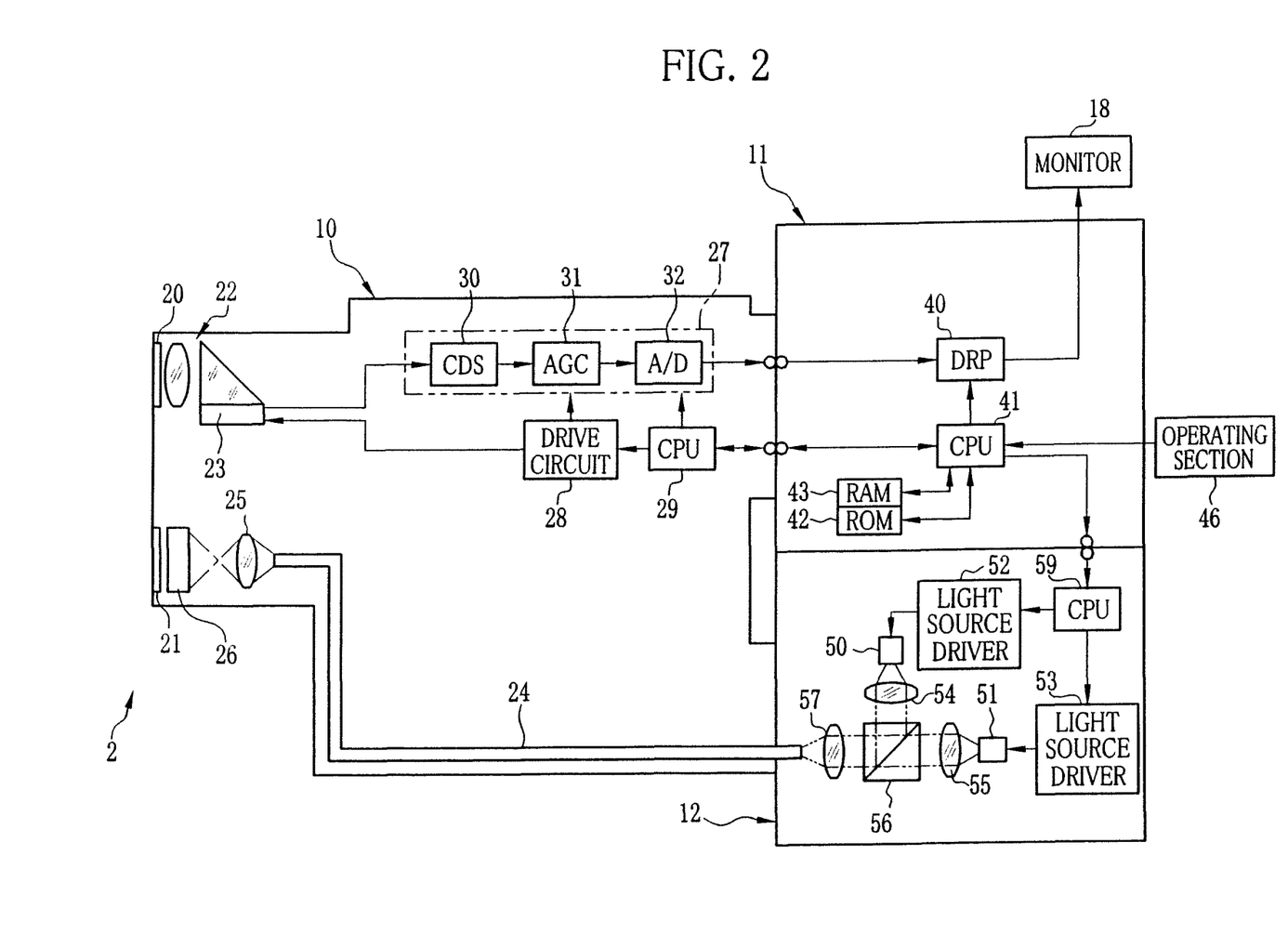
FIG. 2 is a block diagram of the endoscope system.

As shown in FIG. 2, the insertion section 13 has an image-capturing window 20 and an illumination window 21 on the distal end. The image-capturing window 20 is located in front of an objective optics 22 and an imaging device 23. The illumination window 21 is located in front of a wavelength conversion element 26 and a condenser lens 25 to illuminate a diseased site or a site of interest (hereinafter, target site) with illumination light propagated from the light source device 12 through a light guide 24 that extends through the universal cord 16 and the insertion section 13.

Referring back to FIG. 1, the handling section 14 is equipped with various operation members including an angle knob for bending the distal end of the insertion section 13 from side to side and up and down, an air/water button for ejecting air and water from the distal end of the insertion section 13, a shutter release button 17 for capturing a still image of internal body structures, and a zoom button for magnification/reduction of the image on a monitor 18.

On a front side of the handling section 14, a forceps inlet port (not shown) opens to receive the insertion of an electro-surgical knife or other treatment tools. This forceps inlet port is connected to a forceps outlet port (not shown) on the distal end of the insertion section 13 by means of a forceps channel in the insertion section 13.

The endoscope video processor 11 is connected to the electronic endoscope 10 and the light source device 12, and controls the overall operation of the endoscope system 2. The endoscope video processor 11 feeds power to the electronic endoscope 10 using a transmission cable running through the universal cord 16 and the insertion section 13, and also controls the imaging device 23. The endoscope video processor 11 also receives an image signal from the imaging device 23 through the transmission cable, and produces an image by applying various types of processing to the image signal. This image is displayed as an endoscopic image on the monitor 18 connected to the endoscope video processor 11.

As shown in FIG. 2, the electronic endoscope 10 has the image-capturing window 20, the illumination window 21, the objective optics 22, the imaging device 23, the condenser lens 25 and the wavelength conversion element 26 on the distal end of the insertion section 13. The electronic endoscope 10 also has an analog front end circuit (hereinafter, AFE) 27, a drive circuit 28 and a CPU 29 in the handling section 14.

The imaging device 23 is, for example, an interline CCD image sensor or a CMOS image sensor. The imaging device 23 is positioned in such a manner that the image light of the target site that passed through the image-capturing window 20 and the objective optics 22 (composed of a lens group and a prism) strikes an imaging area of the imaging device 23. This imaging area is covered with a color filter composed of different color segments (for example, a primary color filter array in a Bayer arrangement).

The AFE 27 includes a correlation double sampling circuit (hereinafter, CDS) 30, an auto-gain control circuit (hereinafter, AGC) 31 and an analog/digital converter (hereinafter, A/D) 32. The CDS 30 removes reset noises and amplifying noises from the image signal out of the imaging device 23 by correlation double sampling technique. The AGC 31 amplifies this cleaned image signal by the gain factor that the endoscope video processor 11 specifies. The A/D 32 converts the amplified image signal into a digital signal of certain bits. This digital image signal is transmitted to the endoscope video processor 11 by way of the universal cord and the connector 15, and entered into a dynamically reconfigurable processor (hereinafter, DRP) 40.

The drive circuit 28 sends drive pulses (such as, vertical/horizontal scanning pulses and reset pulses) to the imaging device 23 while sending synchronization pulses to the AFE 27. In response to the drive pulse, the imaging device 23 captures an image and generates an image signal. The AFE 27 works in response to the synchronization pulses.

The CPU 29, upon receiving a command from a CPU 41 of the endoscope video processor 11, activates the drive circuit 28 and adjusts a gain factor of the AGC 31.

The CPU 41 controls the overall operation of the endoscope video processor 11. The CPU 41 is connected to every component through a data bus, an address bus and control lines (not shown). Programs (OS, application programs and so forth) and data (graphic data and the like) for controlling the endoscope video processor 11 are stored in a ROM 42. The CPU 41 retrieves necessary programs and data from the ROM 42 to a RAM 43 that is a working memory, and sequentially runs these programs. Additionally, the CPU 41 collects examination-related information, such as an examination date, patient's information, operator's information and other texture information, through an operating section 46 and LAN (Local Area Network), and stores it in the RAM 43.

Under the control of the CPU 41 (reconfiguration controller), the DRP 40 applies appropriate processing to the image signal in accordance with the type of illumination light used. More specifically, the DRP 40 applies various types of signal processing and image processing, including color separation, color interpolation, gain correction, white balance adjustment, gamma correction, electronic magnification, color emphasis and edge highlight, and produces an image. The resultant image is transmitted to a display control section 93 (see, FIG. 4) of the DRP 40.

Figure 4:
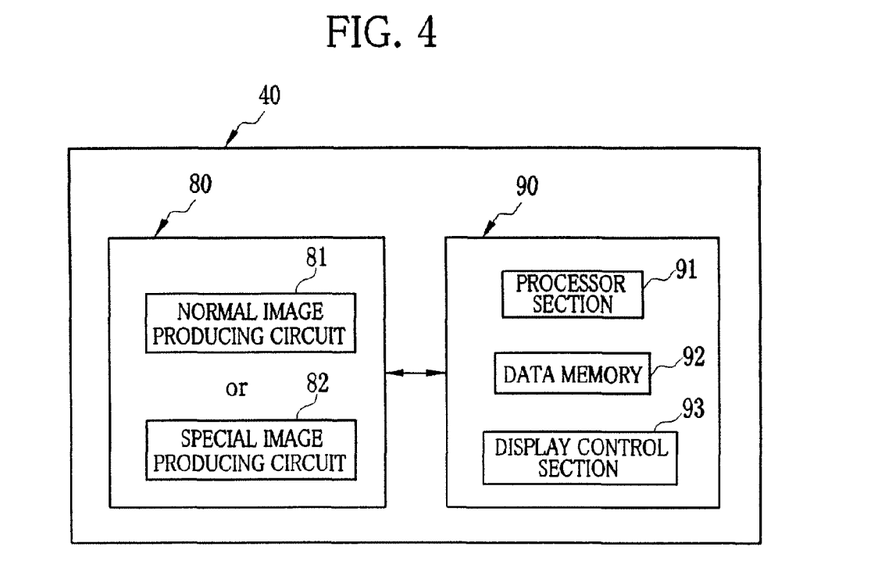
FIG. 4 is an explanatory view illustrating each section of the DRP.

The display control section 93 receives the graphic data of the ROM 42 and the RAM 43 from the CPU 41. This graphic data contains a display mask that covers a part of an internal body image corresponding to ineffective pixels, the above-mentioned texture information and graphical user interface (GUI). The display control section 93 performs a display controlling process, such as superimposing of the display mask, the texture information and the GUI, and a layout process. Finally, the internal body image is displayed on the monitor 18.

The operating section 46 includes an operation panel on a case of the endoscope video processor 11, operation buttons and switches on the handling section 14 of the electronic endoscope 10, a mouse and a key board and other usual input devices. In response to an instruction made on the operating section 46, the CPU 41 activates each component.

The endoscope video processor 11 also includes a compression circuit for compressing an image in a given format (for example, JPEG format), a media interface (I/F) for storing the compressed images in a CF card, a magnetic optical disc (MO), a CD-R or a similar removable medium, and a network I/F for controlling data transmission to the LAN. These components are connected to the CPU 41 through the data bus and the like.

The light source device 12 includes a blue laser source (first laser source) 50 for emitting a blue laser beam at a peak wavelength of 445 nm, a near-ultraviolet laser source (second laser source) 51 for emitting a near-ultraviolet laser beam at a peak wavelength of 375 nm, collimator lenses 54, 55 for collimating the laser beams from the blue laser source 50 and the near-ultraviolet laser source 51, an optical path combiner 56 for combining the light paths of the two laser beams, and a condenser lens 57 in front of the optical path combiner 56. A CPU 59 controls light source drivers 52, 53 to turn on and off the blue laser source 50 and the near-ultraviolet laser source 51.

While the blue laser source 50 and the near-ultraviolet laser source 51 are selectively turned on, the emitted laser beams pass through the optical path combiner 56, and are guided by the condenser lens 57 to an entrance end of the light guide 24. The light guide 24 transmits the incident laser beams to the distal end of the insertion section 13 of the electronic endoscope 10. The light guide 24 may be, for example, a bundle of quartz optical fibers tied with a tape.

Near an exit end of the light guide 24, the condenser lens 25 is placed. Locate in front of the condenser lens 25 is a wavelength conversion element 26 made from first and second wavelength conversion materials. Actually, the wavelength conversion element 26 is a piece of block in which several phosphors are dispersed. The first wavelength conversion material includes phosphors that absorb a part of the blue laser beam from the blue laser source 50 and emits green to yellow luminescence by fluorescence (namely, laser-induced luminescence). By combining the blue laser beam and the green to yellow luminescence, a white light beam, or normal illumination light, is produced.

The second wavelength conversion material includes a phosphor that absorbs a part of the laser beam from the near-ultraviolet laser source 51 and emits green luminescence. This type of phosphor may be, for example, a green phosphor LiTbW208 (see, Tsutomu ODAKI, "Phosphor for White LED", IEICE Technical Research Report ED2005-28, CFM2005-20, SDM2005-28, pp. 69-74 (2005-05)) or a beta-sialon blue phosphor (see, Naoto HIROSAKI, "Temperature dependence of oxynitrides/oxynitride phosphors for white light-emitting diodes", Extended abstracts of the 53rd meeting of the Japan Society of Applied Physics). In the wavelength conversion element 26, the phosphors of the first and second wavelength conversion materials are randomly dispersed. The random dispersion, however, is not mandatory, and any variation may also be applicable in accordance with the nature of the phosphors. For example, the first and second wavelength conversion materials may be segmented into micro-blocks, which are then joined together.

The combination of the green to yellow luminescence of the first wavelength conversion material and the blue laser beam, or the normal illumination light (white light), is emitted forwards in the optical path while the blue laser source 50 is turned on. The narrow-bandwidth green or blue luminescence of the second wavelength conversion material, or the special illumination light, is emitted while the near-ultraviolet laser source 51 is turned on.

The endoscope system 2 can work in three operating modes; a normal capture mode that uses only the normal illumination light, a special capture mode that uses only the special illumination light and a simultaneous observation mode that uses the normal and special illumination light interchangeably. These modes are switched through the operating section 46.

In the normal capture mode, the CPU 41 controls the light source drivers 52, 53 by way of the CPU 59 to turn on the blue laser source 50 and turn off the near-ultraviolet laser source 51. The blue laser beam is transmitted through the light guide 24 to the wavelength conversion element 26, which combines the green to yellow illumination of the first wavelength conversion material with the blue laser beam to produce the white light (normal illumination light). The target site is thus illuminated by the normal illumination light.

In the special capture mode, on the other hand, the CPU 41 turns off the blue laser source 50 and turn on the near-ultraviolet laser source 51. The second wavelength conversion material of the wavelength conversion element 26 absorbs a part or whole of the near-ultraviolet laser beam, and emits the narrow-bandwidth green or blue light (special illumination light). The target site is thus illuminated by the special illumination light.

In the simultaneous observation mode, the CPU 41 turns on the blue laser source 50 and the near-ultraviolet laser source 51 interchangeably at charge-storage time intervals of the imaging device 23. The target site is thus illuminated alternately by the normal illumination light and the special illumination light at the charge-storage time intervals. Instead, only the near-ultraviolet laser source 51 may be turned on and off at the charge-storage time intervals while the blue laser source 50 is kept on.

The DRP 40 has an ability to change the circuit arrangement in a single clock interval. Even during the processing, the DRP 40 dynamically reconfigures the circuit arrangement, and becomes a totally different circuit. This type of processor is available in the market, and an example is DAP-DNA (product name: from IPFlex Inc.).

Figure 3:
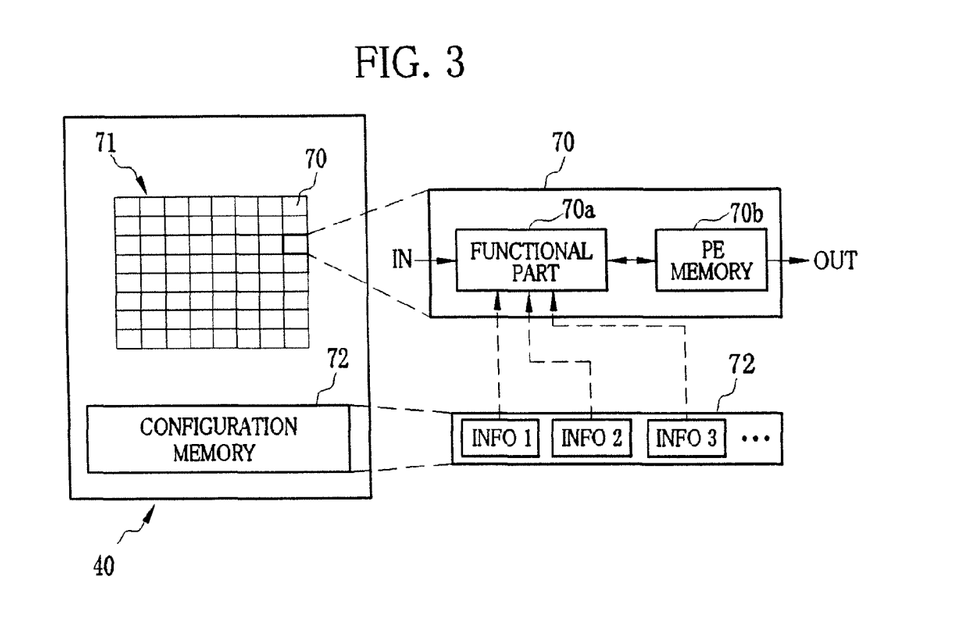
FIG. 3 is an explanatory view illustrating the structure of a DRP.

As shown in FIG. 3, the DRP 40 includes a PE matrix 71 where a plurality of processor elements (hereinafter, PE) 70 are arranged in matrix. Each PE 70 is composed of a functional part 70a for computation and a PE memory 70b for storing the computation results of the functional part 70a. The arithmetic operation of the functional part 70a (addition, subtraction, logical operation and the like) is dynamically changeable. A connection (IN/OUT) between the PEs 70, or interconnection of the PEs 70 is also dynamically changeable.

The DRP 40 also includes a configuration memory 72, which stores different types of circuit information. The connection between the PEs 70 and the operation of the functional part 70a of each PE 70 are determined (defined) according to the circuit information selected. By switching the circuit information, the function of the DRP 40 can be changed.

As shown in FIG. 4, the DRP 40 of this embodiment is provided with a reconfigurable region 80 and a common region 90. The reconfigurable region 80 is configurable between two or more different circuits at the charge-storage intervals (every single field period) of the imaging device 23, and performs different operations to different types of images. The common region 90 is fixed, and performs the same operation to any types of images. The reconfigurable region 80 and the common region 90 are configured in the PE matrix 71 by defining the connection between the PEs 70 and the operation of the functional part 70a based on the circuit information selected from the configuration memory 72.

The reconfigurable region 80 is configurable between a normal image producing circuit 81 and a special image producing circuit 82. The normal image producing circuit 81 processes the image signals having been obtained under the normal illumination light, and the special image producing circuit 82 processes the image signals having been obtained under the special illumination light. These image producing circuits 81, 82 perform different image processing operations each tailored for a specific type of the illumination light, and produce the different internal body images. Hereafter, the image obtained with the normal light is referred to as a normal image, and the image obtained with the special light is referred to as a special image.

The common region 90 is configured into a processor section 91, a data memory 92 and the display control section 93. The processor section 91 is provided for maintaining continuity between the images (fields), and calculates a difference between two successive fields for camera shake correction. The data memory 92, which is composed of the PE memories 70b in the PE matrix, overwrites and stores the image data. The processor section 91 retrieves the image data from the data memory 92 for camera shake correction and other operations.

The display control section 93 controls the monitor 18 to display only the normal images in the normal capture mode and only the special images in the special capture mode. In the simultaneous observation mode, display control section 93 displays the normal and special images side by side on the monitor 18 (see, FIG. 6).

Since the reconfigurable region 80 and the common region 90 are both configured in the PE matrix 71, all the process steps from the image processing to the display control can be performed by a single processor (i.e., DRP 40). The circuitry for the image processing can therefore be minimized. Additionally, only the DRP 40 needs to be accessed during the image processing, and it is possible to speed up the entire operation.

Figure 5:
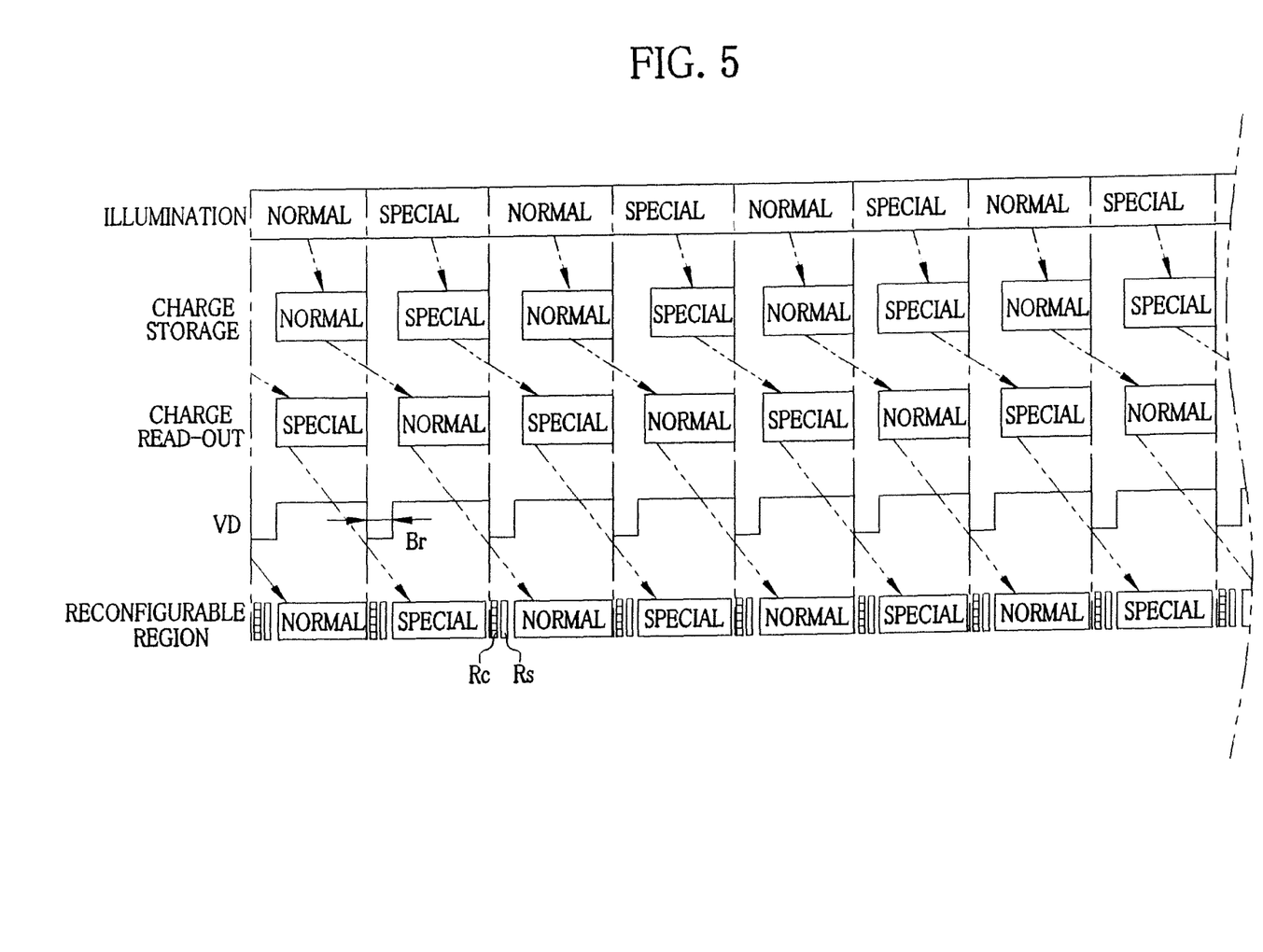
FIG. 5 is a timing chart illustrating the sequence from image capture to image processing in a simultaneous observation mode.

Described hereinafter, with reference to a timing chart of FIG. 5, is the sequence from the image capture to the image processing in the simultaneous observation mode. First of all, under the normal illumination light, the imaging device 23 stores (or accumulates) electrical charges that correspond to the image of the target site. After the lapse of the charge-storage time, the electrical charges are readout from the pixels of the imaging device 23. During this period, the normal illumination light is switched to the special illumination light.

The image signal from the imaging device 23 is transmitted to the DRP 40 by way of the AFE 27. At this time, the reconfigurable region 80 of the DRP 40 is configured to the normal image producing circuit 81, which performs the appropriate image processing for the normal illumination light and produces the normal image.

Upon radiation of the special illumination light, the imaging device 23 stores electrical charges that correspond to the image of the target site under the special illumination light. After the lapse of the charge-storage time, the electrical charges are read out from the pixels, and the special illumination light is switched to the normal illumination light.

The charge read-out operation is controlled by vertical/horizontal synchronization signals which the drive circuit 28 provides. The image signal of the imaging device 23 is not read out while the vertical synchronization signal (VD) stays at a zero level (vertical blanking interval Br). Accordingly, there is no need to perform the image processing during the vertical blanking interval Br. The DRP 40 is reconfigured in this vertical blanking interval Br.

The vertical synchronization signal is transmitted from the drive circuit 28 to the CPU 41 of the endoscope video processor 11 by way of the CPU 29 of the electronic endoscope 10. When detecting that the vertical synchronization signal falls to zero level, the CPU 41 gains access to the DRP 40. The DRP 40, upon receiving a command of the CPU 41, loads the circuit information from the configuration memory 72. Then, based on the circuit information, the DRP 40 reconfigures the operation of the functional part 70a of each PE 70 and the connection of the PEs 70 (shown as Rc in the drawings) to switch between the normal image producing circuit 81 and the special image producing circuit 82 in the reconfigurable region 80.

After the reconfiguration, the DRP 40 resets the PE memories 70b to reset the internal data. This reset process prevents carry-over of the internal data, which causes malfunction of the PEs 70.

At this time, the processor section 91 and the display control section 93 in the common region 90 of the DRP 40 are not reconfigured. The data memory 92 is reset as necessary. In other words, a certain function of the DRP 40 (i.e., reconfigurable region 80) is changed, while the remaining function (i.e., the common region 90) is unchanged and carried over.

In particular, the CPU 41 loads from the configuration memory 72 the circuit information for only the PEs 70 of the reconfigurable region 80, and reconfigures these PEs 70 only. The circuit information for the common region 90, on the other hand, is loaded only once at the beginning. Alternatively, it is possible to load the circuit information for one of the image producing circuits 81, 82 for the PEs 70 of the reconfigurable region 80, and fixed circuit information for the PEs 70 of the common region 90 each time. This method requires simpler control, and is more preferable than the former method.

The special image producing circuit 82 refers to the information that is stored (during the normal image processing period) in the data memory 92 through the processor section 91, and performs various types of processing appropriate for the special light to generate the special image.

Repeating the above mentioned sequence allows switching between the normal illumination light and the special illumination light at the charge-storage time intervals of the imaging device, and switching of the normal image producing circuit 81 and the special image producing circuit 82. As a result, the target site can be observed under the normal light and the special light at substantially simultaneously. Although the common region 90 is configured in the DRP 40 in this embodiment, the function of the common region 90 may be provided outside the DRP 40.

Figure 6:
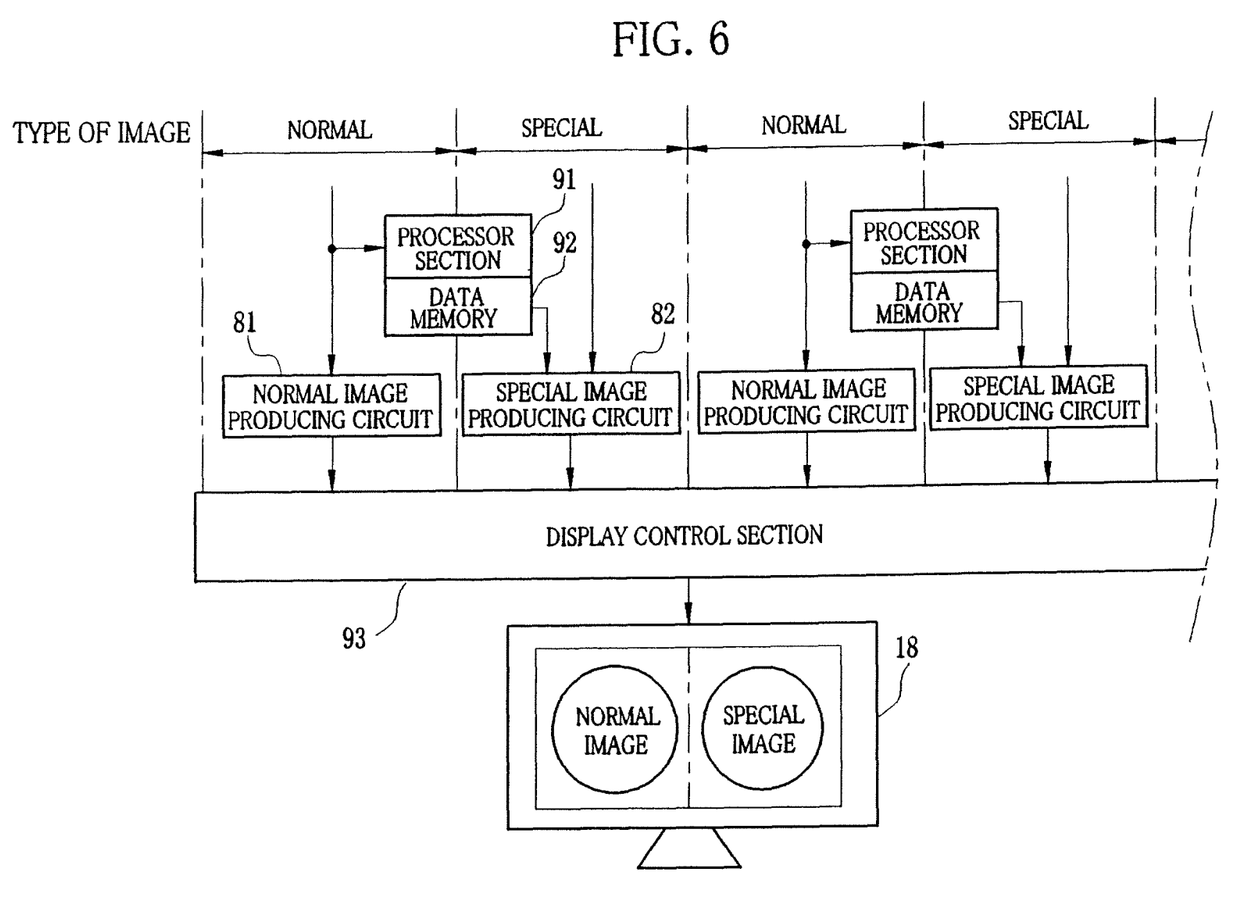
FIG. 6 is a view illustrating a flow of the image processing in the DRP.

Hereinafter described, with reference to FIG. 6, is a flow of the image processing that DRP 40 performs in the simultaneous observation mode. The normal image producing circuit 81 is the first to perform the image processing operation for producing the normal image. At the same time, the processor section 91 executes the process to maintain continuity between the normal and special images. The resultant data of the processor section 91 is stored in the data memory 92. The normal image is transmitted to the display control section 93. Then, the special image producing circuit 82 performs the image processing operation, with reference to the data of the data memory 92. The special image is transmitted to the display control section 93.

The display control section 93 converts the normal image data and the special mage data into video signals (such as component signals or composite signals) compatible with the monitor 18. These video signals are transmitted to the monitor 18, which displays the normal image and the special image side by side. Since there is only one filed difference between the normal and special images, they can be regarded as simultaneously-captured images.

Next, the operation of the endoscope system 2 is described. First of all, the electronic endoscope 10 is plugged into the endoscope video processor 11 and the light source device 12, which are then turned on. The patient information and then the examination start command are entered through the operating section 46.

The insertion section 13 is inserted into a patient's body. Under the normal capture mode, the CPU 41 of the endoscope video processor 11 controls the light source drivers 52, 53, by way of the CPU 59 of the light source device 12, to illuminate the target site with the normal illumination light. Additionally, the reconfigurable region 80 of the DRP 40 is configured to the normal image producing circuit 81, and is never reconfigured to the special image producing circuit 82. Accordingly, all the fields are processed by the normal image producing circuit 81, and the monitor 18 displays only the normal images.

Under the special capture mode, by contrast, the CPU 41 controls the light source drivers 52, 53 to illuminate the target site with the special illumination light. The reconfigurable region 80 of the DRP 40 is configured to the special image producing circuit 82, and is never reconfigured to the normal image producing circuit 81. Accordingly, all the fields are processed by the special image producing circuit 82, and the monitor 18 displays only the special images.

Under the simultaneous observation mode, the CPU 41 controls the light source drivers 52, 53 to illuminate the target site alternately with the normal illumination light and the special illumination light at the charge-storage time intervals of the imaging device 23.

At the same intervals, the reconfigurable region 80 of the DRP 40 is reconfigured alternately between the normal and special image producing circuits 81, 82. After each reconfiguration, the PE memory 70b of each PE 70 is cleared to reset the data. At this time, the processor section 91 and the display control section 93 of the common region 90 are not reconfigured. Additionally, the data for the next image processing is kept in the data memory 92. In this manner, the image producing circuits 81, 82 produce the normal and special images, which are displayed side by side on the monitor 18.

As above described, the normal and special images are obtained at substantially the same time with a small circuit by reconfiguring the DRP 40 at the charge-storage time intervals. Displaying the normal and special images side by side on the monitor 18 facilitates comparison of these images, and allows for strict comparison of these images in the medical examination.

Figure 7:
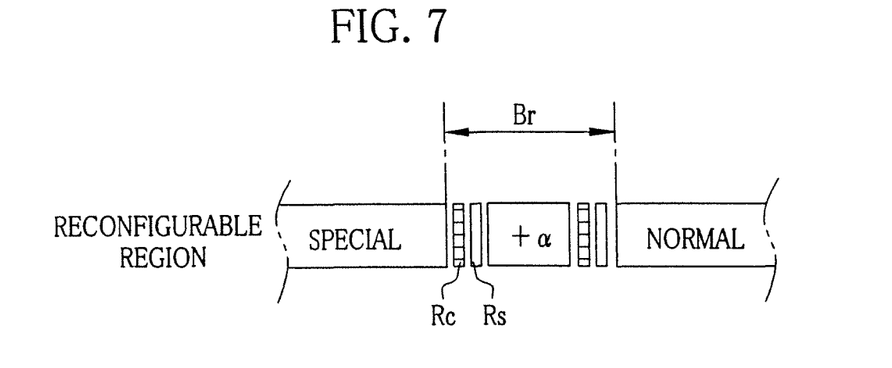
FIG. 7 is a view illustrating a sequence of reconfiguration of a reconfigurable region.

Although the endoscope video processor 11 of the above embodiment only executes the reconfiguration operation on the reconfigurable region 80 and the data reset operation on the PE memories 70b in the vertical blanking interval Br, it may be possible to execute one or more different operations, such as an operation "+α" in FIG. 7, in the vertical blanking interval Br. An example of this operation "+α" may be table calculation using parameters retrieved from a look up table (LUT). The calculation using the LUT may be, for example, the calculation for adjusting the luminance of the normal and special illumination light based on the luminance level of an image.

In executing a different operation during the vertical blanking interval Br, the reconfigurable region 80 is firstly reconfigured, and an additional processing section is configured in the PE matrix 71. Then, the PE memories 70b are cleared to reset the data, and the different operation is executed. Upon finishing this different operation, the reconfigurable region 80 is reconfigured again and the PE memories 70b are cleared to configure the next image producing circuit (the normal image producing circuit 81 in FIG. 7) within the PE matrix 71. This method allows for further reducing the size of the circuit.

Although the reconfiguration and resetting operations are performed in the vertical blanking interval in the above embodiment, they may be done in synchronization with switching signals that the light source device 12 generates to switch the normal illumination light and the special illumination light. In this instance, the CPU 41 of the endoscope video processor 11 and the CPU 59 of the light source device 12 are configured to transmit the switching signals.

Figure 8:
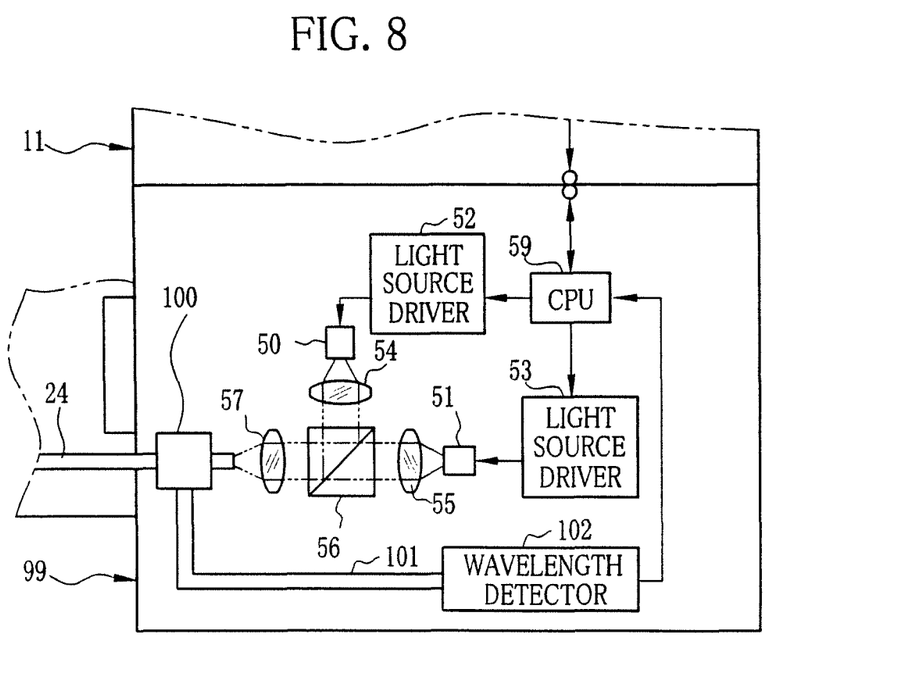
FIG. 8 is a block diagram of a light source device, according to another embodiment, for synchronizing the reconfiguration with changes in wavelength of the illumination light.

Alternatively, the switching of the illumination light may be monitored by detecting the wavelength of the illumination light so as to perform the reconfiguration and resetting operations in synchronization with the switching of the illumination light. This can be implemented with a light source device 99, shown in FIG. 8, which includes an optical splitter 100 and a wavelength detector 102. The optical splitter 100 separates a part of the illumination light in the light guide 24, and sends it to the wavelength detector 102 through a light guide 101. The wavelength detector 102 detects the wavelength of the illumination light, which is then transmitted to the CPU 41 of the endoscope video processor 11 by way of the CPU 59. This configuration allows for synchronizing the reconfiguration and resetting operations with the switching of the illumination light.

The normal and special images are not necessarily displayed side by side in the simultaneous observation mode. For example, it may be possible to superimpose a reduced-scale special image on the normal image, which is called picture in picture. Also possible is a multi-monitor system for displaying the normal image and the special image on separate monitor devices.

The light source device for emitting the normal and special illumination light is not limited to the above embodiments, but may be an LED or an LD capable of changing an oscillation wavelength of illumination light in accordance with a drive current. This requires a single light source, and leads to reduce component cost and an installation space.

Figure 9:
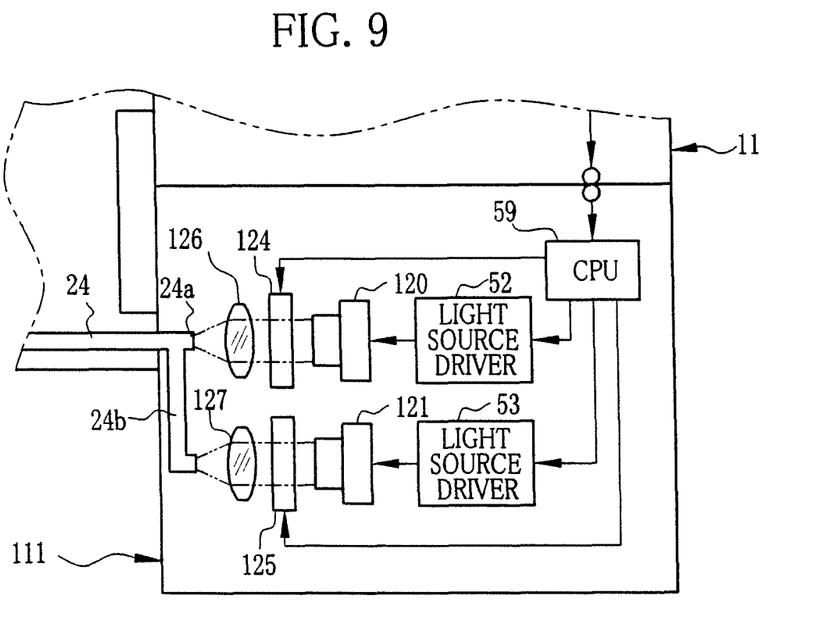
FIG. 9 is a block diagram of another light source device.

A light source device 111, shown in FIG. 9, is also available. The light source device 111 includes two light sources; a normal illumination light source (hereinafter, normal light source) 120 and a special illumination light source (hereinafter, special light source) 121. An exemplary normal light source 120 is a xenon lamp or a white LED (light emitting diode) that emits a broad-wavelength light beam between red and blue (for example, a light beam ranging between 480 nm and 750 nm, or namely normal illumination light). An exemplary special light source 121, by contrast, is a blue LED or an LD (laser diode) that emits a narrow-bandwidth light beam in a certain wavelength range. One or more these diodes are used alone or in combination as the special light source 121 to produce the special light having a wavelength at around 450 nm, 500 nm, 550 nm, 600 nm or 780 nm.

The special light at around 450 nm is suitable for visualizing a microstructure on a target site, such as superficial blood vessels and pit patterns. The special light at around 500 nm is suitable for visualizing a micro-asperity structure, or projections and depressions on the target site. The special light at around 500 nm is well absorbed by hemoglobin, and suitable for visualizing capillaries (minute blood vessels) and redness. The special light at around 600 nm is suitable for visualizing hypertrophy utilizing biological fluorescence. Deep blood vessels are clearly visualized by an intravenous injection of indocyanine green (ICG) or a similar phosphor and the special luminescence at around 780 nm.

The light sources 120, 121 are driven by the light source drivers 52, 53. In front of the light sources 120, 121, there are provided aperture mechanisms 124, 125 that control the luminance of the light beams heading to condenser lenses 126, 127. The condenser lenses 126, 127 focus the light beams across the aperture mechanisms 124, 125 into the entrance end of the light guide 24.

The CPU 59 communicates with the CPU 41 of the endoscope video processor 11, and controls the light source drivers 52, 53 and the aperture mechanisms 124, 125. The illumination lights on the exit end of the light guide 24 is diffused by an illumination lens (not shown) at the tip of the insertion section 13 of the electronic endoscope 10, and emitted through the illumination window 21 to a target site inside a patient's body. In this configuration, the wavelength conversion element 26 is not necessary.

Two light guides 24a, 24b disposed ahead of the light sources 120, 121 are joined into the single light guide 24 within the light source device 111. Similar to the former embodiments, this configuration allows the system to work on different modes: the normal capture mode that uses only the normal light source 120, the special capture mode that uses only the special light source 121, and the simultaneous observation mode that turns on the normal light source 120 and the special light source 121 interchangeably at the charge-storage time intervals of the imaging device 23.

Figure 10:
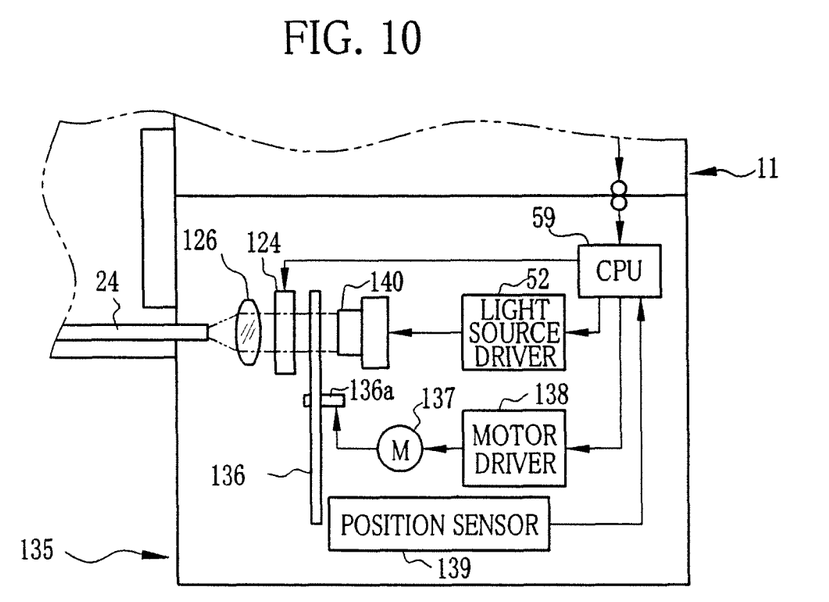
FIG. 10 is a block diagram of yet another light source device.

A light source device 135, shown in FIG. 10, is also available. This light source device 135 has a filter turret 136, a motor 137 coupled to a rotary shaft 136a of the filter turret 136, a motor driver 138 for controlling the motor 137, and a position sensor 139 for detecting a rotational position of the filter turret 136. The light source device 135 also has a halogen lamp as a light source 140.

Figure 11:
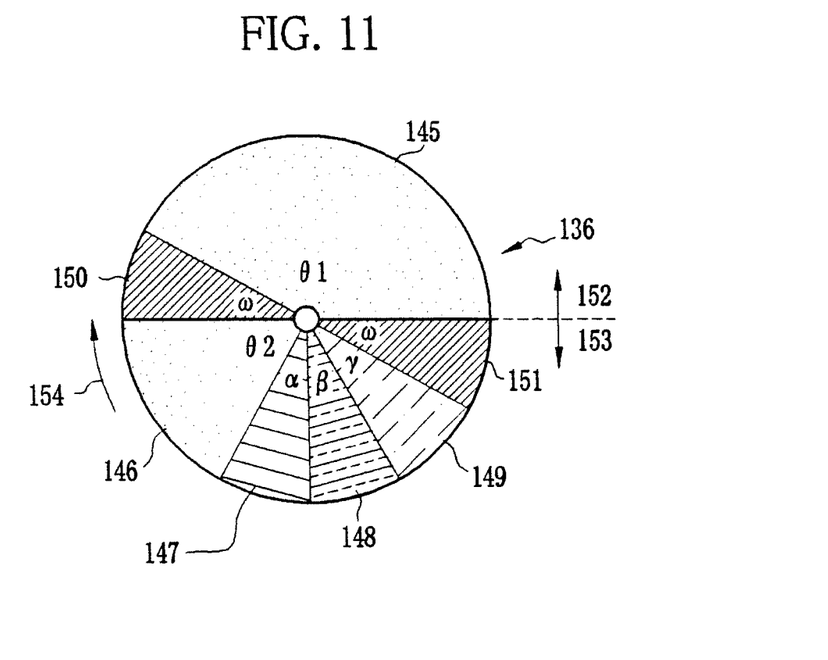
FIG. 11 is an explanatory view illustrating the structure of a filter.

As shown in detail in FIG. 11, the filter turret 136 has a first normal illumination light transmission sector 145, a second normal illumination light transmission sector 146, a blue light transmission sector 147, a green light transmission sector 148, an infrared light transmission sector 149, a first light block sector 150 and a second light block sector 151. Each of the sectors 145 to 151 has its own central angle. The first and second normal illumination light transmission sectors 145, 146 have the central angles of θ1, θ2 (θ1>θ2) respectively, while the blue and green and infrared light transmission sectors 147, 148, 149 have the central angles of α, β and γ respectively. The first and second light block sectors 150, 151 have the same central angle of ω.

The first and second normal illumination light transmission sectors 145, 146 transmit the light components in the white light wavelength band (normal illumination light) from the light source 140. The blue and green and infrared light transmission sectors 147, 148, 149 selectively transmit the narrow-bandwidth light components around 450 nm, 550 nm and 780 nm (special illumination light) within the white light from the light source 140. The special light that passes through the sectors 147 to 149 is half the bandwidth that the RGB pixels of the imaging device 23 respond. The first and second light block sectors 150, 151 correspond to the charge read-out periods and block the illumination light.

The filter turret 136 is divided into a first section 152 and a second section 153. The first light block sector 150 and the first normal illumination light transmission sector 145 are arranged successively in the first section 152 along a rotation direction 154 of the filter turret 136. On the other hand, the second light block sector 151, the infrared light transmission sector 149, the green light transmission sector 148, the blue light transmission sector 147 and the second normal illumination light transmission sector 146 are arranged successively in the second section 153 along the rotation direction 154.

Under the control of the motor driver 138 that drives the motor 137 according to the detection results of the position sensor 139, the filter turret 136 is rotated once every two image capturing operations of the imaging device 23 (i.e., rotated 180 degrees in one image capturing operation). In the course of one image capturing operation, the sectors in the first section 152 or the second section 153 cross in front of the light source 140 to modulate the wavelength, the transmittance and the like of the illumination light that is radiated to the target site.

Figure 12:
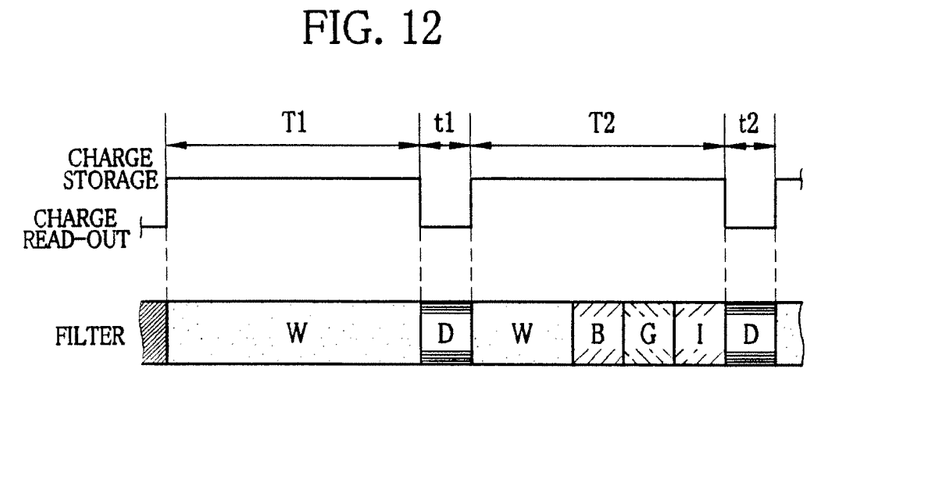
FIG. 12 is a timing chart for operating the imaging device and the filter.

In particular, as shown in FIG. 12, the filter turret 136 is rotated in such a manner that the first normal illumination light transmission sector 145 crosses in front of the light source 140 during a charge-storage time T1, and the first light block sector 150 does the same during a subsequent charge read-out time t1 in a preceding image-capturing operation, and that the blue and green and infrared light transmission sectors 147, 148, 149 successively cross in front of the light source 140 during a charge-storage time T2, and the second light block sector 151 crosses during a subsequent charge read-out time t2 in a succeeding image-capturing operation.

Accordingly, in the preceding image-capturing operation, the signal charges obtained under the normal illumination light are stored (accumulated) in the pixels of the imaging device 23. Then, in the succeeding image-capturing operation, signal charges obtained through the auto-fluorescence of the target site induced by the normal illumination light, the blue light, the green light and the infrared light are stored in the pixels. Hereafter, the image obtained by the preceding image-capturing operation is referred to as a preceding image, and the image obtained by the succeeding image-capturing operation is referred to as a succeeding image.

The preceding image carries the image light of the target site under the normal illumination light, and the succeeding image carries the image light of the target site that emits the luminescence induced by the normal illumination light, the blue light, the green light and the infrared light. The processor section 91 of the DRP 40 extracts R, G and B color components from these two images. By comparison operation of the color components, the processor section 91 calculates a pixel value of each color under the normal illumination light and the special illumination light, and produces the normal image and the special image.

The comparison operation is made using the difference in luminous of the normal illumination light between the first and second normal illumination light transmission sectors 145, 146. For example, the B pixel value of the preceding image is the product of the blue components of the normal light (the image light of the target site) that has passed through the first normal illumination light transmission sector 145. The B pixel value of the succeeding image, by contrast, is the combination of the blue components of the normal light that has passed through the second normal illumination light transmission sector 146 and the blue light that has passed through the blue light transmission sector 147. When the normal illumination light through the first normal illumination light transmission sector 145 has the luminance x times higher than the normal illumination light through the second normal illumination light transmission sector 146, the B pixel value of the blue light can be calculated by multiplying the B pixel value of the preceding image by 1/x, and subtracting this from the B pixel value of the succeeding image.

The G and infrared pixel values can also be calculated by multiplying the pixel value of the preceding image by 1/x, and subtracting this from the pixel value of the succeeding image because, similar to the B pixel value, the G and infrared pixel values of the preceding image are fully made up of the normal light (green light components and infrared light components) that has passed through the first normal illumination light transmission sector 145. The pixel value of each color can be selected as appropriate between the preceding and succeeding images.

The reconfigurable region 80 of the DRP 40 is configured into the normal image producing circuit 81 when processing the image signals obtained through the first section 152, and into the special image producing circuit 82 when processing the image signals obtained through the second section 153.

The luminance of the normal illumination light can be altered between out of the first and second normal illumination light transmission sectors 145, 146 by adjusting at least one of the central angle, or namely dimension of each sector, the time for each sector to cross in front of the light source 140, and the transmission rate of each sector.

The configuration of the filter turret 136 is not limited to the above. For example, the blue light transmission sector 147 may be located in the first section 152, or three or more sections may be provided to use two or more fields in producing the normal and special images.

The filter may be a separate unit that is attachable to the tip of the insertion section 13 of the electronic endoscope 10. With this configuration, the software change is only required for the conventional endoscope systems having a xenon lamp or a similar light source to incorporate the filter of the invention.

While the normal and special images are produced from the successive image signals for at least two fields in the above embodiments, these images may be produced from the image signals extracted at intervals of, for example, several tens of seconds, insofar as the resultant images maintain continuity and appear natural on the display.

Although the target site is illuminated alternately by the normal illumination light and the special illumination light, it may be illuminated alternately by two or more different types of special illumination light. In this instance, the reconfigurable region 80 of the DRP is reconfigured between, for example, first and second special image producing circuits. Additionally, the DRP is target site is illuminated sequentially by the normal illumination light and different types of special illumination light. In this instance, the reconfigurable region 80 is reconfigured among the normal image producing circuit 81 and first and second special image producing circuits.

In the above embodiments, the DRP is reconfigured in the vertical blanking intervals to process the images obtained interchangeably under two or more different types of illumination light. If the DRP is fast enough to process an image before the next image signal is generated, an image memory may be provided between the AFE and the DRP to temporarily store the image out of the AFE. The DRP is thus reconfigured in the time other than the vertical blanking intervals.

While the above embodiments use the electronic endoscope 10 as an endoscope, the present invention provides the same with an ultrasonic endoscope that has one or more ultrasonic transducers on the tip.

Although the present invention has been fully described by the way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
   an imaging device for imaging a site of interest and outputting an image signal, said image device outputting no image signal in a vertical blanking interval;
   a light source device for interchangeably emitting a first and a second illumination light including different spectral characteristics at charge-storage time intervals of said imaging device;
   a dynamically reconfigurable processor including a reconfigurable region to be reconfigured between a first image producing circuit for processing said image signal obtained under said first illumination light to produce a first image and a second image producing circuit for processing said image signal obtained under said second illumination light to produce a second image, wherein reconfiguration of said reconfigurable region is performed in synchronization with interchange of said illumination light;
   a configuration memory for storing circuit information for configuring said first image producing circuit and circuit information for configuring said second image producing circuit;
   a display device for displaying said first and second images side-by-side; and
   a reconfiguration controller for determining a timing of said reconfiguration,
   wherein said reconfiguration controller gains access to said dynamically reconfigurable processor upon detecting said vertical blanking interval, and causes said dynamically reconfigurable processor to load said circuit information for configuring said first image producing circuit or said circuit information for configuring said second image producing circuit from said configuration memory in said vertical blanking interval, so as to reconfigure said reconfigurable region from said first image producing circuit to said second image producing circuit or from said second image producing circuit to said first image producing circuit.

2. The endoscope system of claim 1, wherein said dynamically reconfigurable processor further comprises a common region which applies common processing to said image signals regardless of the type of said illumination light.

3. The endoscope system of claim 2, wherein said common region comprises a display control section for displaying said first and second images on said display device.

4. The endoscope system of claim 2, wherein said dynamically reconfigurable processor comprising:
   a plurality of processor elements whose functions and interconnections are dynamically changeable; and
   a configuration memory for storing a plurality of sets of circuit information which defines different functions and interconnections of said processor elements,
   wherein said reconfigurable region and said common region are configured by selecting a set of circuit information of the plurality of sets of said circuit information and determining the function and interconnection of said processor elements.

5. The endoscope system of claim 2, wherein said common region comprising:
   a processor section for executing a process to maintain continuity between said first and second images; and
   a data memory for storing resultant data of said processor section,
   wherein said dynamically reconfigurable processor generates said second image with reference to said resultant data stored in said data memory when said reconfigurable region is reconfigured to said second image processing circuit.

6. The endoscope system of claim 2, wherein said dynamically reconfigurable processor resets said reconfigurable region after said reconfiguration, and wherein said common region is unchanged after said reconfiguration.

7. The endoscope system of claim 2, wherein said common region is unchanged after said reconfiguration.

8. The endoscope system of claim 1, wherein said dynamically reconfigurable processor resets internal data of said processor elements in said reconfigurable region after said reconfiguration.

9. The endoscope system of claim 1, wherein said reconfiguration controller instructs said reconfiguration and/or resetting of said internal data in response to one of a drive signal for said imaging device and a switching signal of said illumination light.

10. The endoscope system of claim 1, further comprising:
an optical splitter for separating said illumination light in said light source device; and
a wavelength detector for detecting a wavelength of said separated illumination light,
wherein said reconfiguration controller instructs said reconfiguration and/or resetting of said internal data in response to change in wavelength of said illumination light that said wavelength detector detects.

11. The endoscope system of claim 1, wherein said reconfiguration controller instructs said dynamically reconfigurable processor to configure said reconfigurable region into a different circuit for different processing during said reconfiguration between said first and second image processing circuits.

12. The endoscope system of claim 1, wherein said light source device comprises:
a first laser source for emitting a first laser beam having a first wavelength as its center wavelength;
a second laser source for emitting a second laser beam having a second wavelength shorter than said first wavelength as its center wavelength;
an optical path combiner for combining optical paths of said first and second laser beams;
an optical fiber for transmitting said first and second laser beams out of said optical path combiner;
a wavelength conversion element near an exit end of said optical fiber, the wavelength conversion element being excited by said first laser beam to emit first laser-induced luminescence and being excited by said second laser beam to emit second laser-induced luminescence comprising a longer wavelength than said second wavelength in a certain visible spectrum,
wherein said first laser beam is combined with said first laser-induced luminescence to create white light as said first illumination light, and said second laser-induced luminescence comprises a special illumination light as said second illumination light.

13. The endoscope system of claim 12, wherein said first laser source is turned on in a normal image capturing session using said first illumination light, and said second laser source is turned on in a special image capturing session using said second illumination light.

14. The endoscope system of claim 12, wherein a calculation is performed for adjusting a luminance of the special illumination light based on a luminance level of an image during the vertical blanking intervals.

15. The endoscope system of claim 1, wherein said light source device has a normal light source for normal illumination light as said first illumination light and a special light source for special illumination light as said second illumination light.

16. The endoscope system of claim 1, wherein said light source device comprises:

a light source for emitting light containing wavelength components of normal illumination light as said first illumination light and special illumination light as said second illumination light;
a filter turret having one or more normal illumination light transmission sectors and one or more special illumination light transmission sectors, and being disposed in a rotatable manner in an optical path of said illumination light out of said light source; and
a filter driver for rotating said filter turret in synchronization with charge-storage time intervals of said imaging device.

17. The endoscope system of claim 1, wherein said first and second images are simultaneously displayed side-by-side.

18. An endoscope video processor to be used with an endoscope including an imaging device, and a light source device for emitting different types of illumination light interchangeably at charge-storage time intervals of said imaging device to illuminate a site of interest, said endoscope video processor comprising:
a dynamically reconfigurable processor including a reconfigurable region to be reconfigured between several image processing circuits for different signal processing functions, wherein reconfiguration of said reconfigurable region is performed in synchronization with interchange of said illumination light to process said image signals and produce differently illuminated images;
a configuration memory for storing circuit information for configuring said several image processing circuits; and
a reconfiguration controller for determining a timing of said reconfiguration,
wherein said reconfiguration controller gains access to said dynamically reconfigurable processor upon detecting a vertical blanking interval, and causes said dynamically reconfigurable processor to load said circuit information from said configuration memory in said vertical blanking interval, so as to reconfigure said reconfigurable region from said several image processing circuits.

19. A method of driving an endoscope system comprising:
emitting different types of illumination light including different spectral characteristics interchangeably at charge-storage time intervals of an imaging device of an endoscope to illuminate a site of interest;
imaging said site of interest under said illumination light with said imaging device;
outputting no image signal in a vertical blanking interval with said imaging device;
every time said illumination light is interchanged, reconfiguring a reconfigurable region of a dynamically reconfigurable processor to one of several image processing circuits for processing image signals to produce differently illuminated images;
storing circuit information for configuring said several image processing circuits displaying at least two images corresponding to the types of said illumination light side-by-side on a display device; and
determining a timing of said reconfiguration using a reconfiguration controller,
wherein said reconfiguration controller gains access to said dynamically reconfigurable processor upon detecting said vertical blanking interval, and causes said dynamically reconfigurable processor to load said circuit information from said storing circuit information in said vertical blanking interval, so as to reconfigure said reconfigurable region from said several image processing circuits.

\* \* \* \* \*